Oct. 13, 1953 S. F. HAHN Plant Pat. 1,220
SANSEVIERIA PLANT
Filed Aug. 15, 1952
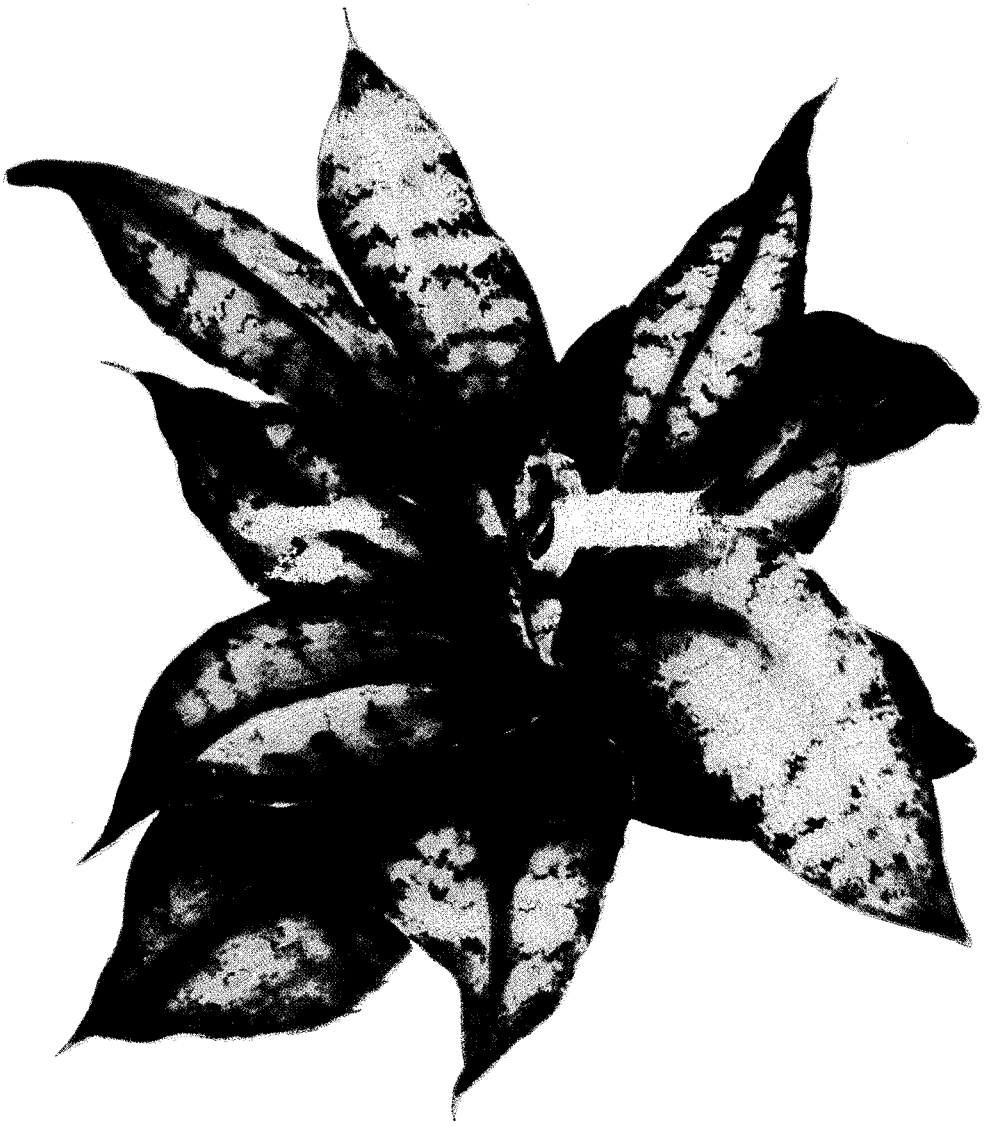
INVENTOR
Sylvan Frank Hahn
By Orville M. Kile
Plant Pat. Agent Patented Oct. 13, 1953

Plant Pat. 1,220

UNITED STATES PATENT OFFICE 1,220

SANSEVIERIA PLANT

Sylvan Frank Hahn, Pittsburgh, Pa.

Application August 15, 1952, Serial No. 304,664

1 Claim. (Cl. 47—59)

My present discovery pertains to a new variety of sansevieria plant. This plant in its habit of spiral or rosette form of growth is identical to the subject of my United States Plant Patent No. 470, but the coloration of the foliage is so singularly different that it constitutes a readily distinguishable and useful new variety. Whereas the coloration and markings of the foliage in Plant Patent No. 470 are typically those of the *Sansevieria zeylonica*, my new plant possesses a metallic silver gray color in its foliage.

This new variety is a sport of the subject of Plant Patent No. 470, known in the trade as Sansevieria Hahnii. It was discovered by me in my greenhouses located in New Orleans, Louisiana.

This variety has been asexually reproduced from both leaf cuttings and suckers (stoloniferous rhizomes which arise from adventitious buds), by me at my greenhouses in New Orleans, Louisiana. It reproduces true to type from either leaf cuttings or suckers.

The illustration accompanying this application gives a view looking downward into the plant. It shows the leaf arrangement and shape as well as the typical foliage coloration as nearly as the artist can portray them, in a plant when two years old. It must be understood, however, that there will be some variation in coloration and markings as between individual specimens of this variety.

In the following detailed description of this new variety, ordinary dictionary color terms are used except where color plates are cited. Such plate references are to Ridgway's Color Standards and Nomenclature.

Growth:

*Type.*—Compact, flat spiral or rosette; base of plant narrow and thin.

*Rapidity.*—Grows and reproduces rapidly and with ease.

*Size.*—Original plant has attained a size of 18 inches after several years' growth.

Leaves:

*Shape.*—Much broader and shorter than other known varieties, except the subject of Plant Patent No. 470 and sports therefrom. Narrow-ovate; very short-pointed on older leaves. Young leaves concave; older leaves flat.

*Size.*—Average size 12 centimeters long by 6 centimeters broad through the center.

*Margin.*—Entire; somewhat undulating.

*Color.*—The entire upper surface of the leaf ranges in color from a dusty silver gray (Mineral Gray, Plate XLVII) to a bright metallic gray. At almost equal intervals along the leaf blade there are indistinct transverse wavy green bands appearing through the silver gray coloration. These are approximately Shamrock Green to Chromium Green, Plate XXXII. On most leaves a distinctively green area, shading from light to dark green, appears along the midrib. However, on all leaves the silver gray is predominant.

*Position.*—Spreading from base; upper one-third horizontal to slightly reflexed.

*Base.*—Narrow.

Flowers: No flowers or fruit have ever been observed, although when the plants grow much older they may have such characters.

Having thus disclosed my discovery, I claim:

A new and distinct variety of sansevieria plant of the spiral or rosette type, substantially as shown and described, characterized particularly by the silver gray coloration over practically the entire leaf area, with other coloration as described; and its ability to faithfully reproduce this color pattern when propagated from both suckers and leaf cuttings.

SYLVAN FRANK HAHN.

No references cited.